(12) United States Patent
Assmann et al.

(10) Patent No.: US 7,091,142 B2
(45) Date of Patent: Aug. 15, 2006

(54) GLASS-CERAMIC AND ITS PRODUCTION AND USE

(75) Inventors: Steffen Assmann, Friedberg (DE); Peter Appel, Woelfersheim (DE); Reinhard Armbrust, Bad Vilbl (DE)

(73) Assignee: Wieland Dental Ceramics GmbH, Rosbach-Rodheim (DE)

( * ) Notice: Subject to any disclaimer, the term of this patent is extended or adjusted under 35 U.S.C. 154(b) by 263 days.

(21) Appl. No.: 10/725,924

(22) Filed: Dec. 3, 2003

(65) Prior Publication Data

US 2005/0277539 A1 Dec. 15, 2005

(30) Foreign Application Priority Data

Feb. 27, 2003 (DE) ................ 103 10 001

(51) Int. Cl.
 *C03C 10/10* (2006.01)
 *A61K 6/02* (2006.01)
 *A61K 13/083* (2006.01)
 *A61C 13/08* (2006.01)

(52) U.S. Cl. .............. 501/6; 501/57; 501/59; 501/64; 501/63; 501/66; 501/68; 501/69; 501/70; 501/72; 501/32; 106/35; 433/202.1; 433/201.1; 433/212.1; 433/206

(58) Field of Classification Search ............ None
See application file for complete search history.

(56) References Cited

U.S. PATENT DOCUMENTS 5,944,884 A   8/1999   Panzera
6,120,591 A   9/2000   Brodkin et al.
6,706,654 B1 * 3/2004  van der Zel ............ 501/32
2002/0198093 A1 12/2002 Van der Zel
2003/0056692 A1 3/2003 Hoshikawa et al.

FOREIGN PATENT DOCUMENTS

| DE | 44 23 793 C1 | 2/1996 |
| DE | 44 28 839 C2 | 2/1996 |
| DE | 197 14 178 A1 | 10/1998 |
| DE | 198 52 516 A1 | 5/2000 |
| EP | 0 690 030 A1 | 1/1996 |
| WO | 99/45888 | 9/1999 |
| WO | 00/10509 | 3/2000 |
| WO | 00/48956 | 8/2000 |

* cited by examiner

*Primary Examiner*—C. Melissa Koslow
(74) *Attorney, Agent, or Firm*—Nath & Associates PLLC; Gary M. Nath; Tanya E. Harkins

(57) ABSTRACT

The invention encompasses a glass-ceramic comprising a continuous glass phase and a crystal phase comprising tetragonal leucite, wherein the glass-ceramic has a crack-free glass phase and a crystal phase comprising leucite crystals distributed essentially homogeneously in the glass phase. The crystal phase has a particle size distribution made of from about 5% to about 70% of a first group of leucite crystals having particle sizes of <1 μm and from about 30% to about 95% of a second group of leucite crystals having particle sizes of ≧1 μm. The proportion of $Li_2O$ in the glass-ceramic is preferably below 0.5% by weight. It is preferred that not only the glass phase but also the crystal phase is essentially free of cracks. The corresponding glass-ceramics are particularly suitable for use in the dental sector, in particular as facing ceramics.

39 Claims, No Drawings

GLASS-CERAMIC AND ITS PRODUCTION AND USE

The invention relates to a glass-ceramic, a process for producing this glass-ceramic and its use for dental purposes.

As is known, glass-ceramics are solids in which both a glass phase and crystalline regions are present. In the microstructure of such glass-ceramics, crystals which form the crystal phase are embedded in one or more glass phases (the glass matrix).

Since the beginning of the 1960s, glass-ceramics have been used for dental purposes, in particular as facing ceramics for coating/facing usually metallic frameworks. For the historical prior art, reference may be made to the two U.S. Pat. Nos. 3,052,982 and 3,052,983 by Weinstein. In these applications, (tetragonal) leucite as crystal phase having a high coefficient of thermal expansion (CTE, from 25° C. to 500° C.) of about $20 \times 10^{-6}$/K is combined with a glass phase which has a low CTE of, for example, about $8 \times 10^{-6}$/K. Selection of the mixing ratios of these components enables different coefficients of thermal expansion of the glass-ceramic to be set in this way.

The use for dental purposes places particular demands on the glass-ceramics, especially in terms of their mechanical stressability. Thus, the leucite forming the crystal phase (secondary phase) represents a potential weak point for cracks or even a predetermined breaking point in the material. Accordingly, crack formation, in particular in the glass phase and also within the crystal phase, is to be avoided. The glass-ceramics having the previously realized microstructures and comprising a glass phase and leucite generally do not achieve this.

Firstly, leucite crystals having a size of up to 60 μm are used in glass-ceramics of this type. Such glass-ceramics frequently have cracks both in the glass phase and also in the crystal phase (leucite phase) because of the large differences in the CTE values of the individual components and because of the comparatively large leucite crystals. The leucite phase in these glass-ceramics is heterogeneously distributed in the glass phase/glass matrix.

In another known group of glass-ceramics, smaller leucite crystals are used. Thus, EP 0 690 030 describes glass-ceramics which comprise not only a leucite phase but also a fluoroapatite phase as further crystal phase, with the leucite crystals present being required to have mean particle sizes of <5 μm. U.S. Pat. No. 5,653,791, too, describes glass-ceramics having particular chemical compositions and containing leucite crystals whose particle sizes do not exceed 10 μm.

Glass-ceramics having relatively small leucite crystals also frequently display a strong tendency to form cracks (both in the glass phase and in the leucite phase) having a size of up to 1 μm. In addition, the leucite crystals of many of these ceramics tend to undergo uncontrolled crystal growth in the case of multiple firings, which once again results in stresses and cracks.

It is therefore an object of the invention to avoid the indicated disadvantages of the glass-ceramics of the prior art. Thus, crack formation in the glass-ceramic should be largely suppressed and even be completely avoided if possible. The corresponding glass-ceramics should, as a result of a substantially optimized microstructure, be particularly suitable for use in the dental sector.

This object is achieved by the glass-ceramic having the features of a continuous glass phase and a crystal phase, comprising tetragonal leucite, wherein the glass phase is free of cracks and the crystal phase comprising leucite crystals is distributed essentially homogeneously in the glass phase and has the following particle size distribution: from about 5% to about 70% of a first group of crystals having particle sizes of <1 μm and from about 30% to about 95% of a second group of crystals having particle sizes of $\geq 1$ μm and the process having the features of mixing the leucite crystals having the appropriate particle size distribution and glass particles with one another, and subjecting the resulting mixture to a heat treatment at temperatures in the range from 700° C. to 1100° C. Preferred embodiments of this glass-ceramic and this process are as follows: an embodiment of the glass-ceramic, wherein the proportion of $Li_2O$ in the composition is <0.5% by weight; a further embodiment of the glass-ceramic, which comprises from 58% by weight to 75% by weight of $SiO_2$, from 8% by weight to 15% by weight of $Al_2O_3$, from 7% by weight to 15% by weight of $K_2O$, from 2% by weight to 12% by weight of $Na_2O$, preferably from 2% by weight to 7% by weight of $Na_2O$ or from 9% by weight to 12% by weight of $Na_2O$, from 0% by weight to 0.4% by weight of $Li_2O$, from 0% by weight to 1% by weight of $Sb_2O_3$, from 0% by weight to 2% by weight of CaO, from 0% by weight to 2% by weight of F, from 0% by weight to 2% by weight of $B_2O_3$, from 0% by weight to 1% by weight of $CeO_2$, from 0% by weight to 0.5% by weight of $P_2O_5$, from 0% by weight to 2% by weight of MgO, from 0% by weight to 2% by weight of BaO; a glass-ceramic according to the present invention, which comprises $\geq 0.1\%$ by weight of $Sb_2O_3$, preferably from 0.1% by weight to 0.5% by weight of $Sb_2O_3$; a further embodiment of the glass-ceramic, which comprises $\geq 0.1\%$ by weight of BaO, preferably from 0.1% by weight to 0.5% by weight of BaO; a further embodiment of the glass-ceramic, which comprises from 0% by weight to 1.5% by weight of CaO, preferably from 0.1% by weight to 1% by weight of CaO; a further embodiemnt of the glass-ceramic which comprises from 0% by weight of F to 1% by weight of F, in particular from 0.1% by weight to 0.4% by weight of F; a further embodiment of the glass-ceramic, which comprises up to 1.0% by weight of $SnO_2$; a further embodiemnt of the glass-ceramic, which comprises up to 1.0% by weight of $TiO_2$; a further embodiment of glass-ceramic, which comprises up to 1.0% by weight of $ZrO_2$; a furhter embodiment of the glass-ceramic, which comprises from 60% by weight to 70% by weight of $SiO_2$, from 10% by weight to 15% by weight of $Al_2O_3$, from 10% by weight to 15% by weight of $K_2O$, from 2% by weight to 7% by weight of $Na_2O$, from 0% by weight to 0.3% by weight of $Li_2O$, from 0.1% by weight to 0.5% by weight of $Sb_2O_3$, from 0.1% by weight to 0.5% by weight of BaO, from 0.5% by weight to 1.0% by weight of CaO, from 0.1% by weight to 0.4% by weight of F; a further embodiment of the glass-ceramic, which comprises the following components from 63% by weight to 67% by weight of $SiO_2$, from 12% by weight to 15% by weight of $Al_2O_3$, from 10% by weight to 14% by weight of $K_2O$, from 2% by weight to 6.5% by weight of $Na_2O$, from 0.1% by weight to 0.2% by weight of $Li_2O$, from 0.1% by weight to 0.3% by weight of $Sb_2O_3$, from 0.1% by weight to 0.3% by weight of BaO, from 0.6% by weight to 1.0% by weight of CaO, from 0.1% by weight to 0.3% by weight of F; yet a further embodiment of the glass-ceramic which comprises the following components from 58% by weight to 65% by weight of $SiO_2$, from 12% by weight to 15% by weight of $Al_2O_3$, from 8% by weight to 12% by weight of $K_2O$ from 9% by weight to 12% by weight of $Na_2O$, from 0% by weight to 0.3% by weight of $Li_2O$, from 0.1% by weight to 0.3% by weight of CaO, from 0% by weight to 0.2% by weight of BaO, from 0.4% by weight to 1.2% by weight of $B_2O_3$, from 0% by weight to 1.0% by weight of $SnO_2$, from 0.1% by weight to 0.5% by weight of F, from 0.2% by weight to 1.0% by weight of $CeO_2$; a further embodiment of the glass-ceramic, wherein from about 5% to about 50%, preferably from about 5% to 35%, in particular from about 5% to about 20%, of crystals of the first group are present; a further embodiment of the glass-ceramic, wherein the crystals of the first group have particle sizes of <0.5 µm, preferably <0.3 µm; a further embodiment of the glass-ceramic, wherein the crystals of the second group have particle sizes of from 1 µm to 10 µm, preferably from 1 µm to 7 µm; a further embodiment of the glass-ceramic, wherein the crystals of the second group consist of more than 50%, preferably more than 80%, of crystals having particle sizes of from 1 µm to 7 µm, and less than 50%, preferably less than 20%, of crystals having particle sizes of >7 µm; a further embodiment of the glass-ceramic, which has the following particle size distribution of the leucite crystals in the glass phase from about 5% to about 50% of crystals of the first group, up to about 1%, preferably up to about 0.5%, of crystals having particle sizes of >7 µm, and the balance, based on 100%, of crystals having particle sizes of from 1 µm to 7 µm; a further embodiment of the glass-ceramic, wherein the crystal phase is essentially free of cracks; a further embodiment of the glass-ceramic which has a coefficient of thermal expansion (CTE at from 25° C. to 500° C.) of from 11 to $16.5 \times 10^{-6}$/K and a firing temperature of from 700° C. to 950° C.; a further embodiment relating to a process for producing the glass-ceramic, which comprises mixing the leucite crystals having the appropriate particle size distribution and glass particles with one another, and subjecting the resulting mixture to a heat treatment at temperatures in the range from 700° C. to 1100° C.; a further embodiment, wherein the heat treatment is carried out at temperatures in the range from 850° C. to 1050° C., preferably at about 1000° C.; a further embodiment wherein the heat treatment is carried out for from 10 minutes to 2 hours, preferably from 30 minutes to 1.5 hours, in particular about 1 hour; a further embodiment, wherein the leucite crystals are prepared as follows: weighing out stoichiometric amounts of the components for the leucite, preferably $K_2O$, $Al_2O_3$ and $SiO_2$, melting the mixture obtained at temperatures of from 1400° C. to 1 600° C., heat-treating the product obtained, preferably at a temperature of about 1000° C. for a period of 1 hour, and comminuting the heat-treated product to the desired particle size distribution, preferably by means of at least one milling step. A novel use of the glass-ceramic is for dental purposes, in particular as dental material and facing tooth replacement, and in particular for metal-ceramic tooth replacement, such as a glass-ceramic coated or faced tooth replacement. The wording of all claims is hereby incorporated by reference into this description.

The glass-ceramic of the invention has a continuous glass phase and a crystal phase comprising tetragonal leucite. The glass phase is free of cracks (according to current understanding based on microscopic examination) and the crystal phase is distributed essentially homogeneously in this glass phase. The leucite crystals in the crystal phase have, according to the invention, a particular particle size distribution, namely from about 5% to about 70% of the leucite crystals have particle sizes of <1 µm and from about 30% to about 95% of the crystals have particle sizes of ≧1 µm.

In contrast to the prior art, leucite crystals which have particle sizes of <1 µm and are consequently in the nanometer size range are present in the glass-ceramic according to the invention. The microstructure of the claimed glass-ceramic can thus also be referred to as a "nanoleucite structure". All of the leucite crystals present are distributed essentially homogeneously in the crack-free glass phase/glass matrix. For the purposes of the present invention, the expression "essentially homogeneous distribution" means that, on average, approximately the same number of leucite crystals are present in equal-sized regions of the glass phase when examined under a microscope/electron microscope.

It should be emphasized that the proportion of $Li_2O$ in the glass-ceramic is preferably below 0.5% by weight. In particular, this proportion is below 0.4% by weight and more preferably in the range from 0% by weight to 0.3% by weight.

For reasons of completeness, it may be mentioned that leucite has the chemical formula $K[AlI_2O_6]$ and is used in its tetragonal structure according to the invention.

The invention is in principle not restricted in respect of the glasses/glass matrix used. According to the invention, particular preference is given to using silicate glasses, in particular glasses having an appreciable proportion of alkali metal ions, i.e. alkali metal silicate glasses.

In a further embodiment, the glass-ceramic of the invention preferably comprises the following components:
from 58% by weight to 75% by weight of $SiO_2$,
from 8% by weight to 15% by weight of $Al_2O_3$,
from 7% by weight to 15% by weight of $K_2O$,
from 2% by weight to 12% by weight of $Na_2O$, preferably from 2% by weight to 7% by weight of $Na_2O$ or from 9% by weight to 12% by weight of $Na_2O$,
from 0% by weight to 0.4% by weight of $Li_2O$,
from 0% by weight to 1% by weight of $Sb_2O_3$,
from 0% by weight to 2% by weight of CaO,
from 0% by weight to 2% by weight of F,
from 0% by weight to 2% by weight of $B_2O_3$,
from 0% by weight to 1% by weight of $CeO_2$,
from 0% by weight to 0.5% by weight of $P_2O_5$,
from 0% by weight to 2% by weight of MgO,
from 0% by weight to 2% by weight of BaO.

In all the amounts given above and below, the percent by weight values are based on the total glass-ceramic.

According to the invention, preference is given to the glass-ceramic containing 0.1% by weight or more of $Sb_2O_3$. Further preference is given to $Sb_2O_3$ contents of from 0.1% by weight to 0.5% by weight.

Preference is likewise given to the glass-ceramic containing 0.1% by weight or more of BaO, preferably from 0.1% by weight to 0.5% by weight of BaO.

In other preferred embodiments of the glass-ceramic of the invention, the glass-ceramic contains from 0% by weight to 1.5% by weight of CaO, in particular from 0.1% by weight to 1% by weight of CaO.

Preference is likewise given to the glass-ceramic having a proportion of F from 0% by weight to 1% by weight, in particular from 0.1% by weight to 0.4% by weight.

Apart from the abovementioned components, it is possible, if desired, for further materials to be present in the glass-ceramic. Thus, preference is given to the glass-ceramic containing up to 1.0% by weight of $SnO_2$, up to 1.0% by weight of $TiO_2$ and/or up to 1% by weight of $ZrO_2$.

Among all the novel glass-ceramics which have been claimed and described, further preference is given to those having particular compositions, since they are particularly useful for dental purposes.

Thus, particular emphasis may be given according to the invention to glass-ceramics which comprise the components:
from 60% by weight to 70% by weight of $SiO_2$,
from 10% by weight to 15% by weight of $Al_2O_3$,
from 10% by weight to 15% by weight of $K_2O$, from 2% by weight to 7% by weight of $Na_2O$,
from 0% by weight to 0.3% by weight of $Li_2O$,
from 0.1% by weight to 0.5% by weight of $Sb_2O_3$,
from 0.1% by weight to 0.5% by weight of BaO,
from 0.5% by weight to 1.0% by weight of CaO,
from 0.1% by weight to 0.4% by weight of F.

Among these, preference is in turn given to glass-ceramics which comprise the following components:
from 63% by weight to 67% by weight of $SiO_2$,
from 12% by weight to 15% by weight of $Al_2O_3$,
from 10% by weight to 14% by weight of $K_2O$,
from 2% by weight to 6.5% by weight of $Na_2O$,
from 0.1% by weight to 0.2% by weight of $Li_2O$,
from 0.1% by weight to 0.3% by weight of $Sb_2O_3$,
from 0.1% by weight to 0.3% by weight of BaO,
from 0.6% by weight to 1.0% by weight of CaO,
from 0.1% by weight to 0.3% by weight of F.

Furthermore, emphasis may be given according to the invention to glass-ceramics which comprise the following components:
from 58% by weight to 65% by weight of $SiO_2$,
from 12% by weight to 15% by weight of $Al_2O_3$,
from 8% by weight to 12% by weight of $K_2O$,
from 9% by weight to 12% by weight of $Na_2O$,
from 0% by weight to 0.3% by weight of $Li_2O$,
from 0.1% by weight to 0.3% by weight of CaO,
from 0% by weight to 0.2% by weight of BaO,
from 0.4% by weight to 1.2% by weight of $B_2O_3$,
from 0% by weight to 1.0% by weight of $SnO_2$,
from 0.1% by weight to 0.5% by weight of F,
from 0.2% by weight to 1.0% by weight of $CeO_2$.

In all embodiments of the glass-ceramic of the invention, it is possible for further additives, preferably colorants, in particular pigments, to be added in preferably small amounts to the glass-ceramic. The addition of such pigments is particularly appropriate in the use of the glass-ceramic in the dental sector as addressed below, for example to achieve the various color shades of facing ceramics.

The leucite crystals having particle sizes of <1 μm, which for the purposes of the invention are also referred to as "first group" of crystals, are present in the glass-ceramics claimed in amounts of preferably from about 5% to about 50%, based on all the leucite crystals present. Within this range, preference is given to from about 5% to about 35%, in particular from about 5% to about 20%, of leucite crystals of the first group being present.

In further preferred embodiments of the glass-ceramic of the invention, the leucite crystals of the first group have particle sizes of less than 0.5 μm, in particular less than 0.3 μm.

The leucite crystals having particle sizes of ≧1 μm present according to the invention will, for the purposes of the invention, be referred to as "second group" of crystals. The preferred proportions of the leucite crystals of the second group correspond to the values given above for the preferred proportions of the leucite crystals of the first group. According to the invention, the leucite crystals of the second group preferably have particle sizes in the range from 1 μm to 10 μm, with particle sizes of from 1 μm to 7 μm being further preferred within this range.

In a further embodiment, the leucite crystals of the second group comprise more than 50% of leucite crystals having particle sizes of from 1 μm to 7 μm and less than 50% of leucite crystals having particle sizes of >7 μm. Further preference is given to only a comparatively small proportion of the leucite crystals of the second group having particle sizes of >7 μm. Thus, preferably more than 80%, in particular more than 90%, of the leucite crystals of the second group have particle sizes in the range from 1 μm to 7 μm, and, accordingly, less than 20%, in particular less than 10%, have particle sizes of >7 μm.

In accordance with what has been stated above, a particularly preferred glass-ceramic according to the invention therefore has a particular particle size distribution of the leucite crystals in the crystal phase, namely
from about 5% to about 50% of the leucite crystals have particle sizes of <1 μm (leucite crystals of the first group),
up to about 1%, preferably up to about 0.5%, of the leucite crystals have particle sizes of >7 μm (first part of the leucite crystals of the second group), and
the balance, based on 100% of all the leucite crystals present, of leucite crystals having particle sizes in the range from 1 μm to 7 μm (second part of the leucite crystals of the second group).

In particular embodiments of the invention, not only the glass phase of the glass-ceramic claimed but also the crystal phase (leucite phase) is essentially free of cracks.

The glass-ceramic of the invention preferably has a coefficient of thermal expansion (CTE, from 25° C. to 500° C.) of from 11 to $16.5 \times 10^{-6}$/K and also a preferred firing temperature of from 700° C. to 950° C.

The process of the invention for producing the glass-ceramic claimed comprises mixing the glass particles which form the glass phase/glass matrix, for example particles having $d_{50}$ values of from 2 μm to 20 μm, and leucite crystals having an appropriate particle size distribution with one another. The mixture obtained in this way is then subjected to a heat treatment at temperatures in the range from 700° C. to 1 100° C. Within this temperature range, temperatures in the range from 850° C. to 1 050° C. are preferred for the heat treatment.

The duration of the heat treatment described can essentially be chosen at will. However, the heat treatment is preferably carried out over periods in the range from 10 minutes to 2 hours, preferably from 30 minutes to 1.5 hours. In many cases, further preference is given to the heat treatment being carried out for a period of about 1 hour.

Leucite as can be used in the process of the invention is commercially available. However, it can also be weighed out stoichiometrically in accordance with the above chemical formula and be melted.

A particularly preferred process according to the invention comprises the preparation of the leucite crystals as follows:
weighing out stoichiometric amounts of the components for the leucite, preferably potassium oxide ($K_2O$), aluminum oxide ($Al_2O_3$) and silicon dioxide ($SiO_2$),
melting the stoichiometric mixture obtained at temperatures of from 1 400° C. to 1 600° C.,
heat-treating the fused product, preferably at a temperature of about 1 000° C. for 1 hour,
comminuting the heat-treated product to the desired particle size distribution, preferably by means of at least one milling step.

Of course, the desired particle size distribution can also be obtained by mixing appropriate fractions of leucite crystals.

As already mentioned, the disadvantages of the prior art indicated at the outset are avoided by means of the glass-ceramic of the invention and by means of the process of the invention. As a result of the newly defined microstructure comprising the homogeneous and finely dispersed crystal phase/leucite phase, crack formation in the glass-ceramic is minimized. No cracks whatever occur in the glass phase, and only extremely isolated cracks, if any, occur in the leucite phase. Owing to this microstructure, the glass-ceramic of the invention has very good materials properties, which are also reflected in a smooth surface and a very good polishability of the material.

At this point, the preferably small proportion of $Li_2O$ in the glass-ceramic should be emphasized once again. It has surprisingly been found that the uncontrolled growth of leucite crystals which frequently occurs in multiple firings is greatly reduced at $Li_2O$ contents of <0.5% by weight. Uncontrolled growth can result in stresses in the ceramic which in turn lead to cracks both in the glass matrix and in the crystals themselves. At a low $Li_2O$ content, the crystals in the matrix remain stable.

All these properties make the ceramic of the invention particularly suitable for use in the dental sector. Accordingly, the invention also provides for the use of the glass-ceramic claimed for dental purposes, in particular as dental material. A particularly preferred use of the glass-ceramic claimed is the facing of tooth replacement, in particular for metal-ceramic tooth replacement. These are, as is known, systems in which a basic framework/base body comprising metals or metal alloys is coated or faced with the appropriate glass-ceramic (dental ceramic). The CTE values (from 25° C. to 500° C.) of the glass-ceramic are generally from 0.5 to 2 units below the CTE values of the framework materials. Of course, the glass-ceramic claimed can also be used, for example, as material for inlays, onlays and veneers.

Finally, the invention encompasses the tooth replacement itself which, after its production, comprises a glass-ceramic according to the invention (claim 27). This is, in particular, a metal-ceramic tooth replacement, i.e. generally a base body or a framework comprising a metal or a metal alloy which is coated and/or faced with the glass-ceramic claimed.

Further features of the invention can be derived from the following examples in combination with the subordinate claims. Here, the features and properties presented can be realized either alone or in a combination of a plurality thereof.

EXAMPLE 1

To prepare leucite crystals, $K_2O$, $Al_2O_3$ and $SiO_2$ (quartz) are weighed out in stoichiometric amounts corresponding to the chemical formula $K[AlSi_2O_6]$ and the resulting mixture is melted at 1 500° C. The cool melt is subsequently subjected to a heat treatment at 1 000° C. for a period of 60 minutes. The heat-treated product obtained is then finely milled in a mill until the following particle size distribution is obtained:
  about 20% of leucite crystals in the nanometer range, i.e. <1 μm (first group of leucite crystals),
  about 79% of leucite crystals in the lower μm range from 1 μm to 7 μm (larger part of the second group of leucite crystals), and
  balance, about 1%, of leucite crystals having particle sizes of >7 μm (smaller part of the second group of leucite crystals).

After milling, the finely milled leucite crystals are mixed with glass particles (the glass matrix) in the desired mixing ratio. The silicate glass used (alkali metal silicate glass) is produced by melting the following components at about 1 500° C.:

| | |
|---|---|
| $SiO_2$ | 65.9% by weight |
| $Al_2O_3$ | 14.3% by weight |
| $K_2O$ | 10.5% by weight |
| $Na_2O$ | 8.2% by weight |
| $Li_2O$ | 0.5% by weight |
| CaO | 0.1% by weight |
| $B_2O_3$ | 0.5% by weight. |

The mixed components (leucite crystals, glass matrix) are subsequently subjected to a heat treatment at about 1 000° C. for a period of 60 minutes. A mixing ratio of glass:leucite of, for example, 1:1 results in a glass-ceramic according to the invention having a firing temperature of 900° C. and a CTE (from 25° C. to 500° C.) of $14 \times 10^{-6}$/K. Examination under a microscope/electron microscope shows a crack-free microstructure in which the leucite crystals (leucite phase) are homogeneously distributed in the glass phase. The glass-ceramic is especially suitable as facing ceramic for dental purposes. It displays excellent compatibility with a metal framework, for example a high-gold-content alloy having a CTE in the appropriate range, and can readily be worked in the patient's mouth, for example by polishing.

EXAMPLE 2

In essentially the same way as in example 1, leucite crystals having the following particle size distribution are prepared under different milling conditions:
  about 7% of leucite crystals in the nanometer range, i.e. <1 μm (first group of leucite crystals),
  about 92% of leucite crystals in the lower μm range from 1 μm to 7 μm (larger part of the second group of leucite crystals), and
  a balance, about 1%, of leucite crystals having particle sizes of >7 μm (smaller part of the second group of leucite crystals).

These leucite crystals are mixed in the desired mixing ratio with the glass particles described in example 1 and are heat-treated in the same way. This likewise gives (mixing ratio=1:1) a glass-ceramic according to the invention having a firing temperature of about 900° C. and a CTE (from 25° C. to 500° C.) of $14 \times 10^{-6}$/K. Examination under a microscope/electron microscope shows a crack-free microstructure in which the leucite crystals (leucite phase) are homogeneously distributed in the glass phase. The glass-ceramic is especially suitable as facing ceramic for dental purposes. It displays excellent compatibility with a metal framework, for example a high-gold-content alloy having a CTE in the appropriate range, and can readily be worked in the patient's mouth, for example by polishing.

EXAMPLE 3

An alkali metal silicate glass is produced by melting the following components at about 1 500° C.:

| | |
|---|---|
| $SiO_2$ | 77.8% by weight |
| $Al_2O_3$ | 4.0% by weight |
| $K_2O$ | 3.8% by weight |
| $Na_2O$ | 11.4% by weight |
| $Li_2O$ | 0.2% by weight |
| $Sb_2O_3$ | 0.4% by weight |
| BaO | 0.4% by weight |
| CaO | 1.6% by weight |
| F | 0.4% by weight |

The alkali metal silicate glass prepared in this way is milled to give fine particles. It is subsequently used to prepare a mixture consisting of
- 50% by weight of glass particles having the above composition,
- 48.5% by weight of leucite crystals prepared and finely milled as described in example 1 and
- 1.5% by weight of pigments.

In a manner analogous to example 1, this mixture is subjected to a heat treatment at about 1 000° C. for a period of 60 minutes. This gives a glass-ceramic according to the invention having a firing temperature of 900° C. and a CTE (from 25° C. to 500° C.) of about $13 \times 10^{-6}$/K.

The glass-ceramic is especially suitable as facing ceramic for dental purposes. It displays excellent compatibility with a metal framework, for example a high-gold-content alloy having a CTE in the range from $13.8 \times 10^{-6}$/K to $15.1 \times 10^{-6}$/K, and can readily be worked in the patient's mouth, for example by polishing.

The overall composition of the glass-ceramic produced in this way was determined by X-ray fluorescence analysis. The main constituents are as follows:
- 65.6% by weight of $SiO_2$,
- 13.4% by weight of $Al_2O_3$,
- 12.4% by weight of $K_2O$,
- 5.7% by weight of $Na_2O$,
- 0.1% by weight of $Li_2O$,
- 0.2% by weight of $Sb_2O_3$,
- 0.2% by weight of BaO,
- 0.8% by weight of CaO,
- 0.2% by weight of F.

The invention claimed is:

1. A glass-ceramic comprising a continuous glass phase and a crystal phase, comprising tetragonal leucite, wherein the glass phase is free of cracks and the crystal phase comprising leucite crystals is distributed essentially homogeneously in the glass phase and has the following particle size distribution:
   from about 5% to about 70% of a first group of crystals having particle sizes of <1 μm and
   from about 30% to about 95% of a second group of crystals having particle sizes of ≧1 μm.

2. A glass-ceramic as claimed in claim 1, wherein the proportion of $Li_2O$ in the composition is <0.5% by weight.

3. A glass-ceramic as claimed in claim 1, which comprises the following components:
   from 58% by weight to 75% by weight of $SiO_2$,
   from 8% by weight to 15% by weight of $Al_2O_3$,
   from 7% by weight to 15% by weight of $K_2O$,
   from 2% by weight to 12% by weight of $Na_2O$,
   from 0% by weight to 0.4% by weight of $Li_2O$,
   from 0% by weight to 1% by weight of $Sb_2O_3$,
   from 0% by weight to 2% by weight of CaO,
   from 0% by weight to 2% by weight of F,
   from 0% by weight to 2% by weight of $B_2O_3$,
   from 0% by weight to 1% by weight of $CeO_2$,
   from 0% by weight to 0.5% by weight of $P_2O_5$,
   from 0% by weight to 2% by weight of MgO,
   from 0% by weight to 2% by weight of BaO.

4. A glass-ceramic as claimed in claim 3, which comprises ≧0.1% by weight of $Sb_2O_3$.

5. A glass-ceramic as claimed in claim 3, which comprises ≧0.1% by weight of BaO.

6. A glass-ceramic as claimed in claim 3, which comprises from 0% by weight to 1.5% by weight of CaO.

7. A glass-ceramic as claimed in claim 3, which comprises from 0% by weight of F to 1% by weight of F.

8. A glass-ceramic as claimed in claim 1, which comprises up to 1.0% by weight of $SnO_2$.

9. A glass-ceramic as claimed in claim 1, which comprises up to 1.0% by weight of $TiO_2$.

10. A glass-ceramic as claimed in claim 1, which comprises up to 1.0% by weight of $ZrO_2$.

11. A glass-ceramic as claimed in claim 1, which comprises the following components:
    from 60% by weight to 70% by weight of $SiO_2$,
    from 10% by weight to 15% by weight of $Al_2O_3$,
    from 10% by weight to 15% by weight of $K_2O$,
    from 2% by weight to 7% by weight of $Na_2O$,
    from 0% by weight to 0.3% by weight of $Li_2O$,
    from 0.1% by weight to 0.5% by weight of $Sb_2O_3$,
    from 0.1% by weight to 0.5% by weight of BaO,
    from 0.5% by weight to 1.0% by weight of CaO,
    from 0.1% by weight to 0.4% by weight of F.

12. A glass-ceramic as claimed in claim 1, which comprises the following components:
    from 63% by weight to 67% by weight of $SiO_2$,
    from 12% by weight to 15% by weight of $Al_2O_3$,
    from 10% by weight to 14% by weight of $K_2O$,
    from 2% by weight to 6.5% by weight of $Na_2O$,
    from 0.1% by weight to 0.2% by weight of $Li_2O$,
    from 0.1% by weight to 0.3% by weight of $Sb_2O_3$,
    from 0.1% by weight to 0.3% by weight of BaO,
    from 0.6% by weight to 1.0% by weight of CaO,
    from 0.1% by weight to 0.3% by weight of F.

13. A glass-ceramic as claimed in claim 1, which comprises the following components:
    from 58% by weight to 65% by weight of $SiO_2$,
    from 12% by weight to 15% by weight of $Al_2O_3$,
    from 8% by weight to 12% by weight of $K_2O$,
    from 9% by weight to 12% by weight of $Na_2O$,
    from 0% by weight to 0.3% by weight of $Li_2O$,
    from 0.1% by weight to 0.3% by weight of CaO,
    from 0% by weight to 0.2% by weight of BaO,
    from 0.4% by weight to 1.2% by weight of $B_2O_3$,
    from 0% by weight to 1.0% by weight of $SnO_2$,
    from 0.1% by weight to 0.5% by weight of F,
    from 0.2% by weight to 1.0% by weight of $CeO_2$.

14. A glass-ceramic as claimed in claim 1, wherein from about 5% to about 50% of crystals of the first group are present.

15. A glass-ceramic as claimed in claim 1, wherein the crystals of the first group have particle sizes of <0.5 μm.

16. A glass-ceramic as claimed in claim 1, wherein the crystals of the second group have particle sizes of from 1 μm to 10 μm.

17. A glass-ceramic as claimed in claim 1, wherein the crystals of the second group consist of more than 50% of crystals having particle sizes of from 1 μm to 7 μm, and less than 50% of crystals having particle sizes of >7 μm.

18. A glass-ceramic as claimed in claim 1, which has the following particle size distribution of the leucite crystals in the glass phase:
    from about 5% to about 50% of crystals of the first group,
    up to about 1% of crystals having particle sizes of >7 μm, and
    the balance, based on 100%, of crystals having particle sizes of from 1 μm to 7 μm.

19. A glass-ceramic as claimed in claim 1, wherein the crystal phase is essentially free of cracks.

20. A glass-ceramic as claimed in claim 1 which has a coefficient of thermal expansion (CTE at from 25° C. to 500° C.) of from 11 to $16.5 \times 10^{-6}$/K and a firing temperature of from 700° C. to 950° C.

21. A process for producing a glass-ceramic as claimed in claim 1, which comprises mixing the leucite crystals having the appropriate particle size distribution and glass particles with one another, and subjecting the resulting mixture to a heat treatment at temperatures in the range from 700° C. to 1100° C.

22. The process as claimed in claim 21, wherein the heat treatment is carried out at temperatures in the range from 850° C. to 1050° C.

23. The process as claimed in claim 21 or claim 22, wherein the heat treatment is carried out for from 10 minutes to 2 hours.

24. A tooth replacement, in particular a metal-ceramic tooth replacement, which cimprises a glass-ceramic as claimed in claim 2, in particular is coated of faced with such a glass-ceramic.

25. A glass-ceramic as claimed in claim 3, wherein the $Na_2O$ is present in an amount of 2% by weight to 7% by weight.

26. A glass-ceramic as claimed in claim 25, wherein the $Na_2O$ is present in an amount of from 9% by weight to 12%.

27. A glass-ceramic as claimed in claim 4, wherein the $Sb_2O_3$ is present in an amount of from 0.1% by weight to 0.5% by weight.

28. A glass-ceramic as claimed in claim 5, wherein the BaO is present in an amount of from 0.1% by weight to 0.5%.

29. A glass-ceramic as claimed in claim 6, wherein the CaO is present in an amount of from 0.1% by weight to 1% by weight.

30. A glass-ceramic as claimed in claim 7, wherein the F is present in an amount from 0.1% by weight to 0.4% by weight.

31. A glass-ceramic as claimed in claim 14, wherein from about 5% to 35% of crystals of the first group are present.

32. A glass-ceramic as claimed in claim 31, wherein from about 5% to about 20% of crystals of the first group are present.

33. A glass-ceramic as claimed in claim 15, wherein the crystals of the first group have particle sizes of <0.3 μm.

34. A glass-ceramic as claimed in claim 16, wherein the crystals of the first group have particle sizes of from 1 μm to 7 μm.

35. A glass-ceramic as claimed in claim 17, wherein the crystals of the second group consist of more than 80% of crystals having particle sizes of from 1 μm to 7 μm and less than 20% of crystals having particle particle sizes of >7 μm.

36. A glass-ceramic as claimed in claim 18, wherein up to about 0.5% of the crystals have particle sizes of >7 μm.

37. The process according to claim 22, wherein the heat treatment is carried out at temperatures in the range of about 1000° C.

38. The process according to claim 23, wherein the heat treatment is carried out from 30 minutes to 1.5 hours.

39. The process according to claim 37, wherein the heat treatment is carried out for about 1 hour.

* * * * *